United States Patent [19]
Takai et al.

[11] Patent Number: 4,816,486
[45] Date of Patent: Mar. 28, 1989

[54] AMIDE DERIVATIVES AND 5-LYPOXYGENASE INHIBITORS CONTAINING THE SAME

[75] Inventors: Makoto Takai, Hachioji; Noriie Itoh, Hino; Shin Hattori, Yokohama; Hirokazu Hasegawa, Tokyo; Toshio Wakabayashi, Tama, all of Japan

[73] Assignee: Terumo Corporation, Tokyo, Japan

[21] Appl. No.: 912,261

[22] Filed: Sep. 29, 1986

[30] Foreign Application Priority Data

Sep. 27, 1985 [JP] Japan ................................ 60-214195

[51] Int. Cl.⁴ .......................................... A61K 31/165
[52] U.S. Cl. ..................................... 514/620; 564/170
[58] Field of Search ......................... 564/170; 514/620

[56] References Cited

U.S. PATENT DOCUMENTS

| | | | |
|---|---|---|---|
| 3,192,213 | 6/1965 | Krapcho | 564/170 X |
| 3,268,407 | 8/1966 | Hoffmann | 564/170 X |
| 4,536,346 | 8/1985 | Shepherd et al. | 564/170 X |
| 4,562,201 | 12/1985 | Stout et al. | 564/170 X |
| 4,661,505 | 4/1987 | Marshall et al. | 564/170 X |

FOREIGN PATENT DOCUMENTS 505970  10/1981  Spain ................................. 564/170

OTHER PUBLICATIONS

Chemical Abstracts 99:5360W (1983).

*Primary Examiner*—Glennon H. Hollrah
*Assistant Examiner*—Carolyn S. Greason
*Attorney, Agent, or Firm*—Cushman, Darby & Cushman

[57] ABSTRACT

Novel amide derivatives are disclosed. As examples of said amide derivatives are mentioned N-cyclohexyl-N-methyl-(2-(3-(3-methoxy-4-hydroxyphenyl)-2-(propenoylamino)-3, 5-dibromobenzyl)amine and N-cyclohexyl-N-methyl-(2-(5-(3-methoxy-4-hydroxyphenyl)-2,4-pentadienoylamino )-3,5-dibromobenzyl)amine. These amide derivatives have a 5-lipoxygenase inhibitory activity and are useful as an antiallergic agent.

3 Claims, No Drawings

AMIDE DERIVATIVES AND 5-LYPOXYGENASE INHIBITORS CONTAINING THE SAME

BACKGROUND OF THE INVENTION

1. Field of the Invention

The present invention relates to amide derivatives and 5-lypoxygenase inhibitor containing the same.

The amide derivatives provided by the invention are novel compounds which possess an activity inhibiting the action of 5-lypoxygenase and are useful as an antiallergic agent.

2. Prior Arts

Recent investigations have elucidated that leucotriene $C_4$ ($LTC_4$) and leucotriene $D_4$ ($LTD_4$) are synthesized in vivo from arachidonic acid by the action of 5-lypoxygenase, and these leucotrienes are allergy-inducing factors (Science 320, 568(1983)).

As a result of extensive studies on a variety of amide derivatives and their 5-lypoxygenase-inhibiting activities, we have found that certain amide derivatives have a potent 5-lypoxygenase-inhibiting activity and are useful as an antiallergic agent. The present invention is based upon the above finding.

SUMMARY OF THE INVENTION

It is an object of this invention to provide amide derivatives represented by the general formula (I)

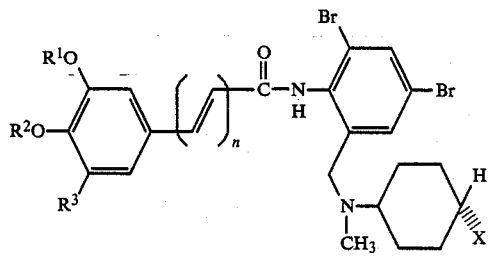

wherein $R^1$ and $R^2$ which may be the same or different represent hydrogen atoms or lower alkyl groups, $R^3$ represents a hydrogen atom or a lower alkoxy group, X represents a hydrogen atom or a hydroxy group and n is an integer of 1 or 2.

A further object of the invention is to provide 5-lypoxygenase inhibitors containing an amide derivative represented by the above formula (I).

DETAILED DESCRIPTION OF THE INVENTION

The lower alkyl group as defined for the substituent in the above-mentioned formula (I) means a straight or branched-chain alkyl group containing 1–4 carbon atoms. Methyl, ethyl or propyl is preferred. The lower alkoxy group means a straight or branched alkoxyl group containing 1–4 carbon atoms. Methoxy, ethoxy or propoxy is preferred.

The amide derivatives represented by the above-mentioned formula (I) are produced by reacting a reactive derivative of a carboxylic acid represented by the formula (II)

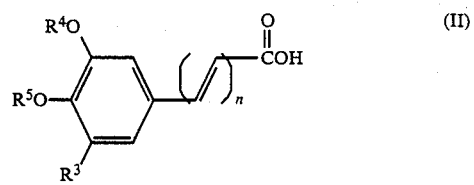

wherein $R^3$ and n have the same meanings as defined above and $R^4$ and $R^5$ which may be the same or different and represent hydroxy-protective groups or lower alkyl groups with an amine derivative represented by the formula (III)

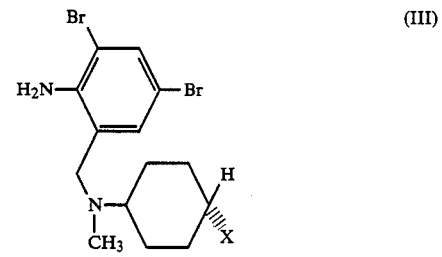

wherein X has the same meaning as defined above, and if required, removing the hydroxy-protective groups.

As the above-mentioned reactive derivative of the carboxylic acid (II) is preferably employed a halide, for example, chloride or bromide, or an anhydride of said carboxylic acid. As the hydroxy-protective group is preferably employed an aliphatic or aromatic acyl group such as acetyl, propionyl, benzoyl or toluoyl; or benzyl group. The above-mentioned reaction is carried out by a method known per se. For example, the reactive derivative of the carboxylic acid (II) is dissolved in an appropriate organic solvent such as, for example, chloroform, the amine derivative (III) is added to the solution, and the mixture is reacted at room temperature for several hours. After completion of the reaction, the desired product (I) is isolated from the reaction mixture by a conventional method and purified by such a means as column chromatography.

When $R^4$ and/or $R^5$ in the above formula (II) is a hydroxy-protective group, the protective group is removed by a conventional method. For example, when the protective group is an acyl group, deacylation is effected by the treatment with a mineral acid such as hydrochloric acid. When the protective group is benzyl group, the removal is effected by a catalytic reduction.

The amide derivatives of the invention are useful as a lypoxygenase inhibitor and are administered for the therapy and prevention of diseases such as allergic asthma and allergic rhinitis. The dose is variable depending upon patient's conditions, but is generally 10–2000 mg, and preferably 20–600 mg per day for an adult. It may be administered in one to three divided doses in a day as needed depending upon patient's conditions. Route of administration may be in any suitable form, and oral administration is particularly desirable. Intravenous administration is also feasible.

The compound of the invention may be administered either alone or in admixture, as one of the active ingredients, with pharmaceutical carriers or excipients, by employing conventional procedures, in a variety of forms such as tablets, sugar-coated tablets, powders, capsules, granules, suspension, emulsion and injectable solution. Examples of the carriers or excipients are calcium carbonate, calcium phosphate, starch, glucose, lactose, dextrin, alginic acid, mannitol, talc, and magnesium stearate.

Examples and a test example are given to illustrate the invention in more details, but the invention is not limited thereto in any way.

EXAMPLE 1

To a suspension of 200 mg (0.703 mmol) of 3-(3-methoxy-4-benzyloxyphenyl)-2-propenic acid in dry chloroform (6 ml) was added 178.5 mg (1.406 mmol) of oxalyl chloride in the atmosphere of argon at room temperature. The mixture was stirred for one hour, and the reaction mixture was concentrated under reduced pressure. To the residue thus obtained was added dry chloroform (4 ml) followed by addition of a solution of 264 mg (0.703 mmol) of brmohexine in dry chloroform (2 ml), and the solution was stirred for 3 hours. To the reaction mixture was added saturated aqueous solution of sodium hydrogen carbonate followed by extraction with chloroform. The organic layer was concentrated under reduced pressure, and the residue thus obtained was subjected to column chromatography on silica gel. From the benzene-ethyl acetate (10:1) eluate was obtained 275.8 mg (0.429 mmol) of N-cyclohexyl-N-methyl-(2-(3-(3-methoxy-4-benzyloxy phenyl)-2-propenoylamino)-3,5-dibromobenzyl)amine.

To a solution of 275 mg (0.428 mmol) of the amine compound in acetic acid (3 ml) was added concentrated hydrochloric acid (1.5 ml), and the mixture was stirred at 100° C. for 2 hours and then at room temperature for 14 hours. To the reaction mixture were added ice water and 1N sodium hydroxide to adjust the pH to 8, followed by extraction with ethyl acetate. The organic layer was concentrated under reduced pressure, and the residue was subjected to column chromatography on silica gel. From the benzene-ethyl acetate (5:1) eluate was obtained 134.5 mg (0.243 mmol) of N-cyclohexyl-N-methyl-(2-(3-(3-methoxy-4-hydroxyphenyl)-2-propenoylamino)-3,5-dibromobenzyl)amine. Spectrophotometric data of the product support structure of the formula (IV) shown below.

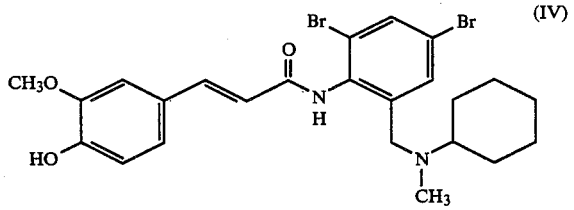

$^1$H-NMR(CDCl$_3$)≡ (ppm): 0.93–2.40(11H, m), 2.11(3H, s), 3.54(2H, bs), 3.88(3H, s), 6.36 (1H, d, J=15.5 Hz), 6.73–7.45 (5H, m), 7,62(1H, d, J=15.5 Hz), 7.68(1H, d, J=2.0 Hz).

IR(KBr)$\nu_{max}^{cm-1}$: 3250, 2930, 2850, 1680, 1620, 1595.

EXAMPLE 2

To a solution of 103.5 mg (0.47 mmol) of 5-(3-methoxy-4-hydroxyphenyl)-2,4-pentadienoic acid in dry tetrahydrofuran (3 ml) was added 119.3 mg (0.94 mmol) of oxalyl chloride in the atmosphere of argon at room temperature. The mixture was stirred for 1.5 hours, and the reaction mixture was concentrated under reduced pressure. To the residue thus obtained was added dry tetrahydrofuran (2 ml) followed by addition of 135 mg (0.36 mmol) of brmohexine in dry tetrahydrofuran (2 ml) at room temperature. The mixture was stirred with heating under reflux for 2 hours and at room temperature for 14 hours. To the reaction mixture was added saturated aqueous solution of sodium carbonate followed by extraction with ethyl acetate. The organic layer was concentrated under reduced pressure, and the residue thus obtained was subjected to column chromatography on silica gel. From the benzene-ethyl acetate (10:1) eluate was obtained 140.8 mg (0.24 mmol) of N-cyclohexyl-N-methyl-(2-(5-(3-methoxy-4-hydroxyphenyl)2,4-pentadienoylamino)-3,5-dibromobenzyl)amine. Spectrophotomethic data of the product support structure of the formula (V) shown below.

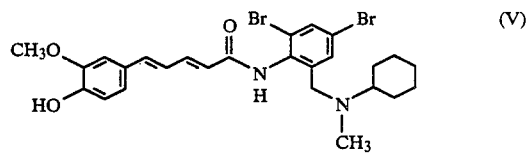

$^1$H-NMR(CDCl$_3$)δ (ppm): 1.06–2.35(11H, m), 2.10(3H, s), 3.51(2H, bs), 3,88(3H, s), 6.00 (1H, d, J=15.0 Hz), 6.50–7.75 (8H, m), 7.66(1H, d, J=2.0 Hz). IR(KBR)$\nu_{max}^{cm-1}$: 3210, 2920, 2840, 1650, 1605, 1580.

IR(KBr)max 3210, 2920, 2840, 1650, 1605, 1580.

TEST EXAMPLE

5-Lypoxygenase-inhibiting Activity

Mouse mastocytoma cells, strain P815 were diluted in a medium containing 90% of the Eagle basal medium (manufactured by Gibco Laboratories) to a cencentration of $5\times10^4$ cells/ml. The diluted liquor was subjected to shake culture in air at 37° C. for 48 hours. The culture liquor was cooled with ice and centrifuged to collect the cells. The cells were re-suspended in a phosphate buffer solution at pH 7.4 to a concentration of $2\times10^7$ cells/ml. The suspension was treated in an ultrasonic cell fragmenting machine and then centrifuged at 10,000 ppm for 10 min. The supernatant was used as the 5-lypoxygenase enzyme solution. To a test tube in which 20 μl of radiolabelled arachidonic acid (10 μ curies/ml), indomethacine ($2\times10^8$ mol) and an amide derivative of the invention to be tested were placed 0.45 ml of phosphate buffer solution, 0.45 ml of the above-prepared enzyme solution and 0.1 ml of 8 mM CaCl$_2$ (calcium chloride) solution. The mixture was reacted at 37° C. for 5 min. After cooled with ice, 60 μl of 1N—HCl (hydrochloric acid) was added, and the resulting mixture was extracted with 8 ml of ethyl acetate. The extract was concentrated, and the concentrate was spotted and developed on a silica gel thin layer plate (Merck 60F$_{254}$). Determination of the inhibitory activity was made by collecting the portion corresponding to 5-HBTE (5-(s)-hydroxy-6,8,11,14-eicosatetraenic acid) and LTB$_4$ (leucotriene B$_4$), which were 5-lypoxygenase products as detected with a radio-thin layer scanner (Dunnschicht-scanner II LB 2723 manufactured by Berthold), and measuring the radioactivity by means of a scintillation counter. Reduction in the 5-lypoxygenase inhibitory activity is demonstrated by decrease in amount of the 5-lypoxygenase products. As shown in Table 1 below, results of the test indicate high 5-lypoxygenase inhibitory activities. Amide derivatives of the invention not shown in Table I also demonstrated 5-lypoxygenase inhibitory activities.

TABLE I

5-Lypoxygenase Inhibitory activity

| Structural formula | Example | 50% inhibitory concentration IC$_{50}$ (mol) |
|---|---|---|
| 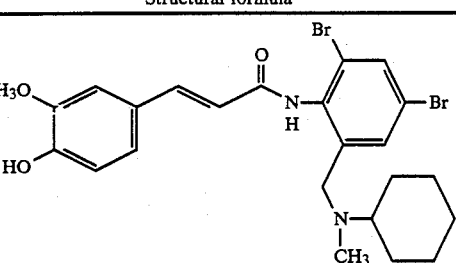 | 1 | $4 \times 10^{-6}$ |
| 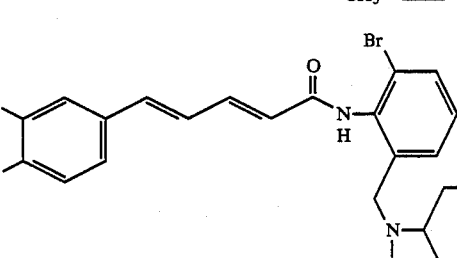 | 2 | $3 \times 10^{-7}$ |

The 50% inhibitory concentration as shown in Table I means concentration of the amide derivative which is required for inhibiting the formation of the abovementioned 5-lypoxygenase products, 5-HETE and LTB$_4$ by 50% of that in the absence of the amide derivative.

Acute Toxicity

An acute toxicity test by oral administration was conducted using ICR male mice (5 weeks old). The LD$_{50}$ value was 300 mg/kg or higher with any of the compounds of the invention thereby confirming higher safety than the effective dose.

What is claimed is:

1. A method of treating allergic condition in a mammal which comprises administering a therapeutically effective amount to such a mammal of an amide derivative represented by the formula

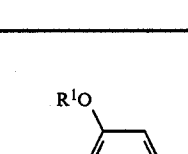

(I)

wherein R$^1$ and R$^2$ which may be the same or different represent hydrogen atoms or lower alkyl groups, R$^3$ represents a hydrogen atom or a lower alkoxy group, x represents a hydrogen atom or a hydroxy group and n is an integer of 1 or 2.

2. A method according to claim 1 in which the compound is one where in R$^1$ represents a lower alkyl group, R$^2$ represents a hydrogen atom and n is an integer of 1 or 2.

3. A method according to claim 1 in which the therapeutically effective amount is 20–600 mg per day for an adult.

* * * * *